United States Patent [19]

Sirén

[11] Patent Number: 5,545,632
[45] Date of Patent: Aug. 13, 1996

[54] METHOD OF TREATING RETROVIRAL DISEASE

[75] Inventor: Matti Sirén, Helsinki, Finland

[73] Assignee: Perstorp AB, Perstorp, Sweden

[21] Appl. No.: 343,239

[22] Filed: Nov. 22, 1994

Related U.S. Application Data

[63] Continuation-in-part of Ser. No. 157,881, Nov. 24, 1993, abandoned, which is a continuation-in-part of Ser. No. 900,129, Jun. 18, 1992, Pat. No. 5,330,979, which is a continuation-in-part of Ser. No. 580,661, Sep. 11, 1990, Pat. No. 5,128,332, which is a continuation-in-part of Ser. No. 492,740, Mar. 13, 1990, Pat. No. 5,015,634, which is a continuation-in-part of Ser. No. 367,968, Jun. 19, 1989, Pat. No. 5,051,411, which is a continuation-in-part of Ser. No. 251,566, Sep. 30, 1988, Pat. No. 5,023,248, which is a continuation-in-part of Ser. No. 173,985, Mar. 28, 1988, Pat. No. 5,019,566, which is a continuation-in-part of Ser. No. 38,230, Apr. 14, 1987, abandoned, which is a continuation-in-part of Ser. No. 15,679, Feb. 17, 1987, Pat. No. 4,797,390, which is a continuation-in-part of Ser. No. 788,801, Oct. 18, 1985, Pat. No. 4,735,936.

[30] Foreign Application Priority Data

Oct. 23, 1984 [SE] Sweden ................... 8405295
Apr. 16, 1986 [SE] Sweden ................... 8601709

[51] Int. Cl.$^6$ ................... A61K 31/66
[52] U.S. Cl. ................... 514/103
[58] Field of Search ................... 514/103

Primary Examiner—Theodore J. Criares
Attorney, Agent, or Firm—Scully, Scott, Murphy & Presser

[57] ABSTRACT

A method of preventing or alleviating retroviral disease by administering to a human or a mammal in need thereof a pharmaceutical composition comprising an amount of at least one specific isomer of inositol triphosphate sufficient to obtain said prevention or alleviation.

6 Claims, No Drawings

METHOD OF TREATING RETROVIRAL DISEASE

REFERENCE TO RELATED APPLICATIONS

This is a continuation-in-part of U.S. patent application, Ser. No. 08/157,881, filed Nov. 24, 1993, now abandoned which is a continuation-in-part of U.S. patent application Ser. No. 07/900,129, filed Jun. 18, 1992, now U.S. Pat. No. 5,330,979, which is a continuation-in-part of U.S. patent application Ser. No. 07/580,661, filed Sep. 11, 1990, now U.S. Pat. No. 5,128,332, which is a continuation-in-part of U.S. patent application, Ser. No. 07/492,740, filed Mar. 13, 1990, now U.S. Pat. No. 5,015,634, which is a continuation-in-part of U.S. patent application, Serial No. 07/367,968, filed Jun. 19, 1989, now U.S. Patent No. 5,051,411, which is a continuation-in-part of U.S. patent application, Ser/ No. 07/251,566, filed Sep. 30, 1988, now U.S. Pat. No. 5,023,248, which is a continuation-in-part of U.S. patent application, Ser. No. 07/173,985, filed Mar. 28, 1988, now U.S. Pat. No. 5,019,566, which is a continuation-in-part of U.S. patent application Ser. No. 07/038,230, filed Apr. 14, 1987, now abandoned, which is a continuation-in-part of U.S. patent application, Serial No. 015,679, filed Feb. 17, 1987, now U.S. Pat. No. 4,797,390, which is a continuation-in-part of U.S. patent application Ser. No. 07/788,801, filed Oct. 18, 1985, now U.S. Pat. No. 4,735,936.

FIELD OF THE INVENTION

The present invention relates to a method of preventing or alleviating different conditions in the body by administering thereto a pharmaceutical composition comprising an amount of at least one specific isomer of inositoltrisphosphate sufficient to obtain said prevention or alleviation.

Acquired immunodeficiency syndrome (AIDS) is a serious immunodeficiency disease induced by human immunodeficiency virus (HIV), type 1 and type 2 (HIV-1 and HIV-2). HIV, which is the aetiological agent for AIDS is a nononcogenic, cytopathic retrovirus of the lentivirus subfamily. Retroviruses have their genetic material in the form of RNA, ribonucleic acid, instead of DNA, deoxyribonucleic acid. In order to turn their RNA into DNA, retroviruses have a special enzyme called reverse transcriptass.

The HIV-virus, 100 nm in diameter is covered by an envelope, and contains a surface glycoprotein as well as an internal cylindrical core. The envelope is formed by phoepholipids and glycoproteins and the core contains the genome and several enzymes.

HIV infects human cells primarily by binding to CD4 receptors on the surface of susceptible cells. This binding is mediated by the oligomeric envelope glycoprotein (gp) of HIV and the receptor on the target cell surface followed by the fusion between the vital envelope and the plasma membrane. The postbinding events which lead to membrane fusion are poorly understood but presumably include a conformational change in the envelope protein which exposes the hydrophopic amino terminus of a gp 41 envelope protein in the fusion reaction.

The binding of the HIV-1 envelope glycoprotein, gp 120, to the cellular receptor is the first step in HIV infection. However, there is also evidence for CD4 independent mechanism of infection. There are reports of HIV infection in a number of CD4-negative cells in vitro (Hareuse, J. M. et al., J. Virol, 63, 2527, 1989, Zachar, V. B. et al. J. Virol, 65, 2102, 1991).

These data show that the expression of CD4 alone is not absolute obligatory and not sufficient to support HIV infection and implies that there are other molecules required for infection.

The patephysiological basis of the profound and irreversible immune depression following the infection is obscure.

AIDS was first recognized in 1981 in young, homosexual men from the U.S. with opportunistic infections, Kaposi's sarcoma, and primary CNS, lymphoma. Although unusual cases of systemic malignant lymphoma were also recognized at that time, statistically significant increases were not apparent until 1985. Victims also suffered from other opportunistic infections, caused by microorganisms that are ubiquitous but ordinarily not able to cause disease. Indeed, the infections and cancers seen in AIDS patients were previously known only in people born with certain defects in their immune system.

Since the disease was first recognized the number of cases have risen swiftly. According to the World Health Organization the increase of AIDS will result in up to 40 million people infected with HIV by the year 2000.

Recently the HIV infection has been classified into three distinct stages: the acute phase, lasting weeks, the chronic phase, lasting years, and the final phase of crisis (generally referred to as AIDS) lasting months to years.

AIDS is an unique disease. No other known infectious disease causes comparable harm by directly attacking the human immune system.

Once in the human body the virus attacks the cells that usually defend the body against infectious discases. These cells include monocytes, macrophages and dendritic cells, so called antigan presenting cells (APC). Furthermore HIV can remain hidden in cells latent for months or years. A third difficulty is that HIV is extraordinary variable in its genetic make-up.

In 1985, zidovudine (AZT) was found to have in vitro activity against the human immunodeficiency virus, HIV. The in vitro and clinical activity of zidovudine is not disputed, but there is considerable debate when to initiate treatment (J. G. Bartlett,: New Engl. J. of Mad., 329, 351, 1993; Cooper D. A. et al.: *New Engl. J. of Mad.*, 329, 297, 1993).

AZT can have serious side effects such as anemia, and in people using the drug, HIV frequently mutates to produce strains that are unaffected by it.

Other nucleoside analoguss are on trial but these will probably only be of limited usage as the mode of action including side effects reassemble those of zidovudine.

The function of AZT is to block the action of the enzyme reverse transcriptass of MIr which stops the virus from replicating in the cells.

Retroviruses vary at a notoriously high rate resulting in rapid appearance of HIV-1 strains which are resistant against drugs and antibodies given to the patient. In addition several other stages in the HIV replicate cycle have been envisioned as targets for therapeutic intervention. One such target is the BIV protease which is essential for the assembly of fully infections HIV particles.

In the past years an intensive search to find effective antiviral therapies has taken place. Active agents that have been discovered during the last years include carbovir (Vince, R. et al: *Biochem. Biophys. Res. Commun.* 156, 1046, 1988), and a class of oxathin benfdic acid esters and derivates (Schultz, R. J., etal.: *Proc. Am. Assoc. Cancer Res.* 33, 409, 1990).

While searching for a new drug which would prevent the spreading of HIV viruses, the following conditions should be fulfilled:

It should have no or few side effects, or at least these side effects should be minimal and tolerable It should have high therapeutic indices It should prevent the prolification of the HIV virus by preventing it from penetrating those cells in which the virus reproduces, or preventing it from reproducing inside these cells.

The half-life of the drug should be long enough to allow and administration once or twice daily.

The compound should be easily identified in the blood in order to establish individual dosage.

The drug should effect the target cell in the same form as it is administered and not only as a result of metabolic activity.

The drug should be teratologically safe.

SUMMARY OF THE INVENTION

According to the present invention it has surprisingly become possible to overcome and reduce the above mentioned disorders as a method of preventing or alleviating these conditions has been brought about. At said method a pharmaceutical composition comprising an amount of at least one specific isomer of inositoltrisphosphate ($IP_3$) sufficient to obtain said prevention or alleviation is administered to a human or an animal.

Preferred embodiments of the invention relate to a method of preventing or alleviating retrovital diseases by administering a pharmaceutical composition comprising an amount of at least one specific isomer of $IP_3$ sufficient to obtain said prevention or alleviation to a human or an animal.

In addition the invention also covers a method of preventing or alleviating acquired immunodeficiency syndrome (AIDS) and AIDS-related diseases by administering a pharmaceutical composition comprising an amount of at least one specific isomer of $IP_3$ sufficient to obtain said prevention or alleviation to a human or an animal.

Furthermore, the invention also covers a method of preventing or alleviating other conditions caused by retroviruses or other enveloped viruses by administering to a human or an animal a pharmaceutical composition comprising an amount of at least one specific isomer of $IP_3$ sufficient to obtain said prevention or alleviation.

From the European Patent No 179439 a pharmaceutical composition comprising as a pharmaceutically active ingredient at least one isomer of inositoltrisphosphate is known. In said patent the effect of this pharmaceutical composition is shown for different areas, such as platelet aggregation.

The production of $IP_3$ and the isolation of the different isomers thereof are disclosed in the U.S. Pat. No. 4.777.134. The $IP_3$ isomers can also be produced by synthetic methods, chemically or enzymatically, starting with e.g. inositol and a phosphorus source. Furthermore, microbiological production methods including hybrid DNA-techniques of $IP_3$ are also suitable.

The structure of $IP_3$ and the different isomers thereof are disclosed in the U.S. Pat. No. 4.735.936 and the U.S. Pat. No. 4.797.390.

It is suitable that the composition used according to the invention exists in unit dosage form. Tablets, granules or capsules are suitable administration forms for such unit dosage. Furthermore, tablets and granules can easily be surface treated such as to provide an enteric coating to prevent an uncontrolled hydrolysis in the stomach and to bring about a desired absorption in the intestine, other suitable administration forms are slow release and transdermal administration, nasal, rectal, intraarticular, topical, intraperitoneal and subcutaneous administrations. A usual pharmaceutically acceptable additive, excipient and/or carrier can be included in the medicament. The tablets or granules can also contain a disintegrant which causes the tablets or the granules, respectively, to disintegrate easily in the intestine. In certain cases, especially in acute situations, it is preferable to use the unit dosage in the form of a solution for intravenous administration. In other situations suspensions comprising the compound can be preferably used as administration form.

The pharmaceutical composition can also consist as such of $IP_3$ solely without any additive, excipient or carrier.

If desired, the composition can be free of other inositol phosphates, $IP_1$, $IP_2$, $IP_4$, $IP_5$ and $IP_6$. Accordingly, the mixture of $IP_3$ isomers can have a purity of 90–100%, such as 93–100% or preferably 95–100%.

Alternatively, the pharmaceutical composition used in the method can consist of or comprise one or more specific $IP_3$ isomors, each present in substantially pure form. Thus, the different isomers can be isolated from each other in substantially pure form, which means than they have a purity of 80–100 %, such as 82–100 % or 85–100 %, preferably 90–100 %. Since the isomers can be produced in pure form they can be mixed in any proportion, of course.

The composition can consist of $IP_3$, wherein said $IP_3$ is provided by at least one of $IP_6$, $IP_5$ or $IP_4$ and a degradative substance such as an enzyme suitable to form $IP_3$.

It is in most cases suitable that the $IP_3$-isomer or isomers in the composition used in the method according to the invention are present in salt form in order not to affect the mineral balance negatively. The salt should preferably consist of a sodium, potassium, calcium zinc or magnesium salt or a mixture of two or more of these salts.

For the above mentioned reasons it is also an advantage if the composition contains a surplus or an extra addition of at least one pharmaceutically acceptable salt of calcium, zinc or magnesium with a mineral acid or organic acid. This is especially valuable for elderly persons who are often deficient in these minerals.

For administration to human patients appropriate dosages can routinely be determined by those skilled in this art by extension of the results obtained in animals at various dosages. The preferred dosage for humans falls within the range of 0.1 to 1000 mg, especially 0.1–200 mg of the compound/day/kg body weight.

The pharmaceutical composition used in the method according to the invention usually contains 0.01–1.5 g, such as 0.05–1.3 g or preferably 0.1–1 g of the compound per unit dosage.

The composition used according to the present invention contains at least one, sometimes two or more of the following substances, which correspond to the essential $IP_3$-isomer or isomer mentioned above:

D-myo-inositol-1,2,6-trisphosphate of the formula

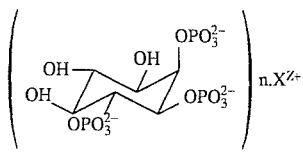

where X is hydrogen, at least one univalent, divalent or multivalent cation, or a mixture thereof, n is the number of ions, and z is the charge of the respective ion; myo-inositol-1,2,3-trisphosphate of the formula

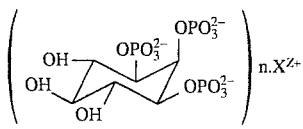

where X, n and z have the above mentioned meaning; L-myo-inositol-1,3,4-trisphosphate of the formula

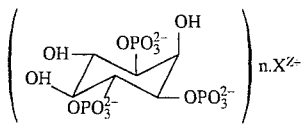

where X, n and z have the above mentioned meaning.

In each of the above formulas n ranges between 6 to 1 inclusive and z ranges from 1 to 6 inclusive. Preferably, n is between 3 to 6 inclusive and z is 3, 2 or 1. Of the above isomers D-myo-inosital-1,2,6-trisphosphate is preferred.

Other inositol trisphosphate isomers that may be utilized in the present invention as the active IP$_3$ ingredient in the composition have the structural formula

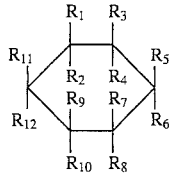  (I)

One group of inositol trisphosphate compound is defined by the structural formula (I) where three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen.

Another group of inositol trisphosphates is defined by the structural formula (I) where three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol trisphosphates is defined by the structural formula (I) where three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol trisphosphates is defined by the structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group of inositol trisphosphates is defined by the structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol trisphosphates is defined by the structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet another group of inositol trisphosphates is defined by the structural formula (I) where three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen.

Finally, another group of inositoltrisphosphates is defined by the structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol trisphosphate compounds within the contemplation of the above formula include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen;

$R_1$, $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$, and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ and $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ end $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$ and $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_3$, $R_5$ and $R_9$ are phosphate, $R_1$, $R_8$ and $R_{12}$ are hydroxyl and $R_2$, $R_4$, $R_6$, $R_7$, $R_{10}$ and $R_{11}$ are hydrogen;

$R_5$, $R_9$ and $R_{12}$ are phosphate, $R_1$, $R_3$ and $R_8$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $r_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_9$ and $R_{12}$ are phosphate, $R_1$, $R_5$ and $R_8$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_9$ are hydroxyl and $R_2$, $R_4$, $R_6$, $R_7$, $R_{10}$ and $R_{11}$ are hydrogen; and $R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen.

The above formula describes specific isomers of inositol trisphosphate where the inositol is selected from the group myoinositol, cisinositol, epiinositol, alloinositol, neoinositol, mucoinositol chiroinositol and scylloinositol. The invention will be further explained in the following examples where Example 1 shows the manufacturing of a solution of $IP_3$ for intravenous administration and Example 2 demonstrates the effect of $IP_3$ to inhibit HIV-induced infection.

EXAMPLE 1

Solution of the sodium salt of D-myo-inositol-1,2,6-trisphosphate ($IP_3$) for injection.

0.5 g of the sodium salt of $IP_3$ and 0.77 g sodium chloride were dissolved in 98.73 ml of water for injection to form a solution suitable for injection into a person or an animal.

EXAMPLE 2

Inhibitory effect of the sodium salt of D-myo-inositol-1,2,6-trisphosphate ($IP_3$) on HIV induced infection.

Five preparations of MT-4 cells (a human T-cell line; $1\times10^6$ cells) were suspended in 500 µl growth medium comprising 10% fetal calf serum and 20 µg/ml gentamicin and 100 IU/ml streptomycin. To four of the suspensions the sodium salt of D-myo-inositol-1,2,6-trisphosphate ($IP_3$) was added to final concentrations of 0.2, 2.0, 20 and 200 µg/ml respectively. The fifth suspension was used as a control with no additions of $IP_3$. 50 µl of HIV-3B (type code of HIV-virus) was added to the suspension followed by an incubation for 2 hours at 37° C. After extensive washing, the infected cells were resuspended in 5 ml growth medium containing appropriate amounts of $IP_3$ in order to reach the final concentrations as mentioned above.

Quadriplicates of the suspensions were transferred to cell culture plates and were cultured for 4 days at 37° C. One measurement of the degree of infection is the expression of the antigen gp-120 on the cells. This HIV-antigen production was measured by an antibody-ELZSA-technique and the results obtained for the different suspensions comprising $IP_3$ were expressed relative to the suspension serving as a control.

The results were normalized and are given in the following table:

| Concentration of $IP_3$ (µg/ml) | Percent infection |
|---|---|
| 0 | 100 |
| 0.2 | 55 |
| 2.0 | 55 |
| 20 | 18 |
| 200 | 0 |

The data demonstrate a significant inhibitory effect of $IP_3$ against HIV-induced infection.

EXAMPLE 3

Viral isolates from HIV-infected patients were used in order to induce an infection by adding peripheral blood mononuclear cells (PBMC) to a medium containing different concentrations of the sodium salt of D-myo-inositol-1,2,6-trisphosphate ($IP_3$). 25 $CCID_{50}$ (50% cell culture infections dose) of PBMCs from HIV-infected patients were incubated with three different concentrations of $IP_3$; 0.125 mg/ml, 0.250 mg/ml and 0.5 mg/ml. A fourth preparation, without any $IP_3$ served as a control. The growth medium consisted of 10% fetal calf serum, 2 µM glutamine, 100 IU/ml penicillin, 100 IU/ml streptomycin and 20 µg/ml gentamicin. The concentration of cells were $2\times10^5$ per ml. All preparations were incubated for 1 hour at 37° C.

PBMCs from healthy donors were then added to the preparation. Before addition, these cells were simulated for three date with phytohemagglutinin (PHA). $0.5\times10^6$ PBA-stimulated PBMCs were added to each preparation, followed by incubation for 3 hours au 37° C. After extensive washing the cells were resuspended in growth medium supplemented with 10 IU/ml of interleukin-2 and seeded in quadruplicates of 100.000 cells in a 96-well microtite plate before further cultivation for 7 days. The HIV-antigen was assayed at the seventh day using an ELISA-technique. The obtained values were normalized and are summarized in the following table:

| Concentration of $IP_3$ mg/ml | HIV-infection (%) |
|---|---|
| 0 | 100 |
| 0.125 | 89 |
| 0.250 | 16 |
| 0.500 | 0 |

In this example, where the HIV-infection is induced by clinical isolates from HIV-infected patients, $IP_3$ shows a strong effect to counteract the infection. At the concentration of 0.5 mg/ml of $IP_3$ the infection is totally abolished.

I claim:

1. A method of treating retroviral disease comprising administering a treatment effective amount of a pharmaceutical composition comprising at least one isomer of inositol triphosphate to a human or other mammal having a retroviral disease.

2. A method according to claim 1 wherein the disease is acquired immuno deficiency syndrome or related disease.

3. A method according to claim 1 wherein the pharmaceutical composition comprises an isomer of inositol triphosphate in salt form.

4. A method according to claim 3 wherein said inositol triphosphate is a salt of sodium, potassium, calcium or zinc.

5. A method according to claim 1 wherein the pharmaceutical composition is in unit dosage forms comprising tablets, granules, capsules, solutions or suspensions.

6. A method according to claim 1 wherein said inositol triphosphate is D-myo-inositol-1,2,6-triphosphate.

* * * * *

UNITED STATES PATENT AND TRADEMARK OFFICE
CERTIFICATE OF CORRECTION

PATENT NO. : 5,545,632
DATED : August 13, 1996
INVENTOR(S) : Matti Siren

It is certified that error appears in the above-indentified patent and that said Letters Patent is hereby corrected as shown below:

Column 1, lines 47-48: "phoepholipids" should read --phospholipids--

Column 1, line 65: "Hareuse" should read --Harouse--

Column 2, line 5: "patephysiological" should read --patophysiological--

Column 2, line 31: "discases" should read --diseases--

Column 2, line 47: "analoguss" should read --analogues--

Column 2, line 52: "transcriptass" should read --transcriptase--

Column 2, line 52: "Mir" should read --HIV--

Column 2, line 59: "BIV" should read --HIV--

Column 2, line 65: "benfdic" should read --benzoic--

Column 2, line 66: "etal." should read --et al.--

Column 5, line 32: "inosital" should read --inositol--

UNITED STATES PATENT AND TRADEMARK OFFICE
CERTIFICATE OF CORRECTION

PATENT NO. : 5,545,632
DATED : August 13, 1996
INVENTOR(S) : Matti Siren

It is certified that error appears in the above-indentified patent and that said Letters Patent is hereby corrected as shown below:

Column 6, line 5: "inositoltrisphosphates" should read --inositol trisphosphates--
Column 6, line 45: "end" should read --and--
Column 7, line 66: "ELZSA" should read --ELISA--
Column 8, line 37: "date" should read --days--
Column 8, line 37: "PBA" should read --PHA--
Column 8, line 40: "au" should read --at--

Signed and Sealed this

Twenty-second Day of April, 1997

Attest:

BRUCE LEHMAN

Attesting Officer

Commissioner of Patents and Trademarks